United States Patent

Chang et al.

[11] Patent Number: 6,037,000
[45] Date of Patent: Mar. 14, 2000

[54] DYE MIGRATION

[75] Inventors: Howard Chang, Madison; Indrajit N. Desai, Succasunna; Arthur Vinen, Florham Park, all of N.J.

[73] Assignee: SmithKline Beecham Corporation, Philadelphia, Pa.

[21] Appl. No.: 08/793,412

[22] PCT Filed: Nov. 15, 1996

[86] PCT No.: PCT/US96/18418

§ 371 Date: May 14, 1998

§ 102(e) Date: May 14, 1998

[87] PCT Pub. No.: WO97/18267

PCT Pub. Date: May 22, 1997

Related U.S. Application Data

[60] Provisional application No. 60/006,769, Nov. 15, 1995.

[51] Int. Cl.[7] .............................. B05D 1/00; C09B 63/00; C09C 3/08
[52] U.S. Cl. .......................... 427/221; 106/272; 106/402; 106/499; 106/502; 106/504; 427/212; 427/215; 427/218; 427/220; 427/374.4; 427/422; 428/402.24; 428/403; 428/407; 424/497; 424/498
[58] Field of Search .................................... 106/402, 499, 106/504, 272, 502; 427/212, 215, 218, 220, 221, 374.4, 422; 428/403, 407, 402.24; 424/497, 498

[56] References Cited

U.S. PATENT DOCUMENTS

| | | | |
|---|---|---|---|
| 4,069,311 | 1/1978 | Mannara | 424/49 |
| 4,129,638 | 12/1978 | Ritze | 264/117 |
| 4,202,879 | 5/1980 | Shelton | 424/66 |
| 4,235,641 | 11/1980 | Engelmann et al. | 106/502 |
| 4,271,211 | 6/1981 | Knepper | 427/195 |
| 4,357,406 | 11/1982 | Kouchi et al. | 430/137 |
| 4,444,746 | 4/1984 | Harvey et al. | 424/49 |
| 4,484,952 | 11/1984 | Bes et al. | 106/504 |
| 4,533,484 | 8/1985 | Walles et al. | 510/152 |
| 4,769,080 | 9/1988 | Clark et al. | 106/402 |

*Primary Examiner*—Anthony Green
*Attorney, Agent, or Firm*—Nora Stein-Fernandez; Janice E. Williams; Charles M. Kinzig

[57] ABSTRACT

The present invention is to a process for producing a matrix particle of a colored lake or dye which matrix reduces the leeching or bleeding of the colored lake or dye into the surrounding medium. The present inventive process is particularly useful in toothpaste formulations.

17 Claims, No Drawings

DYE MIGRATION

This application claims the benefit of U.S. Provisional Application No. 60/006,769, filed Nov. 15, 1995.

FIELD OF THE INVENTION

Process by which colored lakes and dyes are prepared with a material to form dye particles which are impervious to water.

BACKGROUND OF THE INVENTION

Water soluble dyes are generally liquids, or soluble solids which are used in solution. Pigments, are generally solids and are usually insoluble in the medium in which the pigment is being used. Water soluble dyes have significant disadvantages when used in soaps and toothpastes, for instance as these dyes can stain skin, and clothing and often complex with proteinaous materials. Further, as the soap bars and toothpaste contact water repetitively, the water-soluble dyes tend to run and stain sinks, bathtubs, etc. Pigments, are therefore, typically used instead of dyes in applications where color migration or bleeding is undesirable.

Various approaches have been proposed to reduce the bleeding or staining of lakes and dyes to prevent migration of the color into the surrounding phases. These resultant products are used in household and toiletries products such as soap, toothpaste, and other cosmetics.

Absorption of the lake onto a medium, a colorless substrate of alumina, zirconia, or titania in this instance, is taught in U.S. Pat. No. 4,444,746. The alumina, zirconia, or titania is used to absorb the pigment onto their surfaces, which provides a means for dispersion of the color throughout the dentifrice medium, without dissolution of the water-soluble dye.

Water insoluble pigments and production thereof is disclosed in U.S. Pat. No. 4,769,080 in which a layered anion exchange material is contacted with the dye under conditions in which a water-insoluble pigment is obtained. The water soluble dye and the layered anion exchange material are contacted together in a liquid medium in which the dye has been dissolved. The layered anion exchange material is preferably a layered aluminate.

GB Patent 1,319,991 discloses preparation of colored resins with non-toxic water soluble dyes as a water impervious cross-linked synthetic resin for use in toothpastes. The polymerized resins which are used in this process have monomers which are soluble in water and can be polymerized to insoluble resins in an aqueous solution. The resins employed in this disclosure do not take up appreciable water on prolonged contact. Specifically, low molecular weight water soluble resins such as urea formaldehyde, melamine formaldehyde, melamine-urea formaldehyde and phenol formaldehyde resins are described.

U.S. Pat. No. 4,129,638, U.S. Pat. No. 4,202,878, and GB 1,319,992 all disclose preparation of a pigment in an agglomerate form whereby the pigments are dispersed in molten wax, or a gelling agent which is then reduced in particle size to 200 to 500 microns. The pigment particles must be color-fast and water-soluble dyes per se, and can not be used in this invention. However, the disclosure teaches use of color fast dyed thermo-setting resin particles, as described in GB 1,319,991 above.

U.S. Pat. No. 4,069,311 discloses prior art procedures by which speckles have been prepared by melting a physiologically acceptable organic binder, such as a thermoplastic resin, wax or high molecular weight ester, e.g., glyceral tristearte. This prior art method of converting the resultant particles, which are somewhat irregular in appearance and size, to particles in the range of 0.05 to 1 mm can be obtained through tedious and costly screening or sieving. To avoid the irregular shape and screening the patent teaches use of high shear agitation of the speckling material, and a binder, such as thermoplastic resins, gums, gels, paraffin's, waxes, polymers, and higher fatty acids and salts thereof, with dispersion of the molten mixture of binder and dye into a dispersing medium, such as water, thereby forming small globules or particles upon cooling.

Another approach for using non-toxic water soluble dyes is taught in U.S. Pat. No. 4,533,484 in which water-insoluble pigments were produced by contacting the water soluble dye with a polymer comprising an alkyl-2-oxazolidinone moiety. This resulted in a pigment particle have insolubility characteristics of the polymer and color characteristics of the dye. The pigmented polymer is prepared by contacting the polymer with an aqueous medium in which the polymer is at least partially soluble. To this solution, the dyes are added in excess. The temperature is raised and a highly colored precipitate results which may be filtered or dried. The polymer-dye yields a pigment which is insoluble in an aqueous liquid, at temperatures above 3° C. A pigment is generally insoluble in an aqueous medium under normal conditions of use.

The prior art methods have failed to produce a product, particularly a product which has small particle size, which effectively prevents the migration of the color into the surrounding medium. The present invention provides such a method in a commercially practicable, and useful method whereby the prepared matrix particle is useful for any lake of a soluble dye that left untreated would tend to leach in water or other solvent.

SUMMARY OF THE INVENTION

The present invention is to a process for producing a matrix particle of a colored lake or dye which matrix reduces the leeching or bleeding of the colored lake or dye into the surrounding medium.

Another aspect of the present invention is a matrix particle comprised of a substrate and a colored lake or dye having a regular shape and which ingredients are present in a ratio of 0.5 to 9% lake to substrate (w/w).

Another aspect of the present invention is use of the matrix particle in cosmetics or toiletry articles, or for use in coatings of tablets, etc. for pharmaceutical applications.

DETAILED DESCRIPTION OF THE INVENTION

The present invention is to a process for encapsulation of colored lakes within a substrate, such as a high density polyethylene material, which forms particles that are substantially impervious to water, or other solutes of choice. This process results in significantly reduced dye migration of the colored material from the resulting matrix formulation. Optionally, a secondary coating of another substance, such as petrolatum, or similar material may be applied to the matrix particle, wherein dye migration is thereby virtually eliminated.

Suitably, the substrate or encapsulating material, is a high density polyethylene, although, natural and synthetic waxes, such as Carnauba Wax, or microcrystalline wax (Mekon White™ Wax) may be used. Other suitable polymers and waxes that have usefulness in this process include, but are not limited to, other various densities of polyethylene, or oxidized hydrocarbon (such as Petronauba™). To be successfully used as a substrate the agent should have a distinct melting point between about 80° C. to about 130° C. It must be a relatively thin liquid in the molten state, and it must be able to form fine droplets when sprayed from a spray nozzle. It is preferably a solid at room temperature and liquefies without destruction upon heating. The material is preferably hydrophobic. The material is stable in water or other ingredients, such as flavors, glycerin, sorbitol, surfactants and other materials such as are standardly present in dentifrices or tableting for pharmaceuticals. The material is one which can be dispersed in suitable solutes or creams, etc., having been made into a matrix particle with the appropriate lake. Lastly, the material preferably has a "sharp", i.e., highly defined solidification point.

Preferably the encapsulating material is polyethylene, Carnauba Wax, or Mekon White™. More preferably it is a high density polyethylene material. One polyethylene used in the present invention, see Example 1, is Polywax® 500 from Petrolite. This is considered a high density polyethylene, however, it is not of as high a density as the polyethylene used in a "Jet Mill" process, as is described below in another example. Polywax® 500 is a fairly crystalline substance with a sharp melting point of 86 to 88° C. Shown herein, as Example 2, is the substrate polyethylene as Polywax® 500 from Petrolite. In an alternative embodiment the substrate polyethylene as Polywax® 2000 may be utilized, which substrate is completely melted at approx. 130 to 135° C., and has a specification melting point of about 126° C.

As used herein, the term "dye" is an organic species which is essentially water soluble in an aqueous medium, in which the dye remains chemically stable. Suitably, this is a color designated as a Drug and Cosmetic (D&C) color, or is a lake as described in the Handbook of U.S. Colorants for Foods, Drugs, and Cosmetics, D. M. Marmion, Wiley-Interscience Publication, whose disclosure is incorporated by reference herein, and is designated as a Food, Drug and Cosmetic (FD&C) lake or color. Alternatively for use herein mixtures of D&C dyes and FD&C lakes may be used. Preferably, the matrix particles are formed with colored lakes. Preferred lakes include, but are not limited to, FD&C Blue No. 1, Blue No.2, Green No.3, Green No.6, Red No.3, Red No.10, Red No.30 Yellow No.5, Yellow No.6, Yellow No.7, Yellow No.8, and Yellow No.10. Suitable dyes and lakes, their structures, and properties for use herein are well known to those skilled in the art. Further information may be obtained for instance in Kirk-Othmer Encyclopedia of Chemical Technology, 3rd Edition, Volume 6, pg. 561–596 whose disclosure is incorporated by reference herein. Preferred lakes include FD&C Blue No.1 lake, FD&C Green No.3 lake, and D&C Yellow lake No.10.

In one embodiment of this invention the substrate-lake mixture is formed into a matrix particle by applying the method of spray congealing. Spray congealing is an alternative to jet milling and provides for overall lower material cost, a lower energy intensive process as no milling is required to reduce the particle size of the resultant matrix, and is a highly environmentally safe and efficient process. The resultant matrix particles produced by this process, which do not fall within the desired particle size, may simply be reused, or recycled, in the process. There is consequently no effluent, or wash which must be disposed of. As is well known in the art, it is extremely difficult to prevent migration of blue lakes, which makes them also difficult to handle for commercial usage. The present invention therefore provides for an efficient, commercially practical, and environmentally friendly process for production of matrix particles, in particular blue matrix particles, which particles have reduced bleeding, or leaching into the surrounding media.

The resultant particles produced by this process are small and well encapsulated, and require no additional washing phase, as is necessary if a milling process were required. The resultant particles, further, require no milling process to reduce their particle size. The desired particle size (2 to 65, preferably, 5 to 40 microns) is determined by the combination of pumping rate, pressure and nozzle size, as are demonstrated herein.

In spray congealing, the hopper, feed line, and nozzle on the spray dryer are preferably pre-heated. The atomizing air pressure is preferably set between 35 psi to 75 psi. The higher the atomizing pressure, the finer the particle size. As a general rule, it is desirable to spray with the largest fluid cap and the highest possible air pressure available and yet still be able to maintain a fine particle distribution, and be within the cooling capacity of the dryer.

Fan (or flat) spray nozzles can also create fine particles. However, since this set-up uses external mix air caps, it is also most prone to nozzle plugging due to the effects of expansion cooling. Round spray nozzles are considerably less prone to plugging but higher atomization pressures (55 to 75 psi) are generally needed for the round spray nozzle to achieve a fine particle size.

It is possible to produce particles that are too fine (less than 5 microns), using, for instance, an ultrasonic nozzle. The smaller particle size, i.e., "ultra fine" particles, may require more dye to give a suitable color in the desired final product in which they are to be utilized. The smaller particle size encapsulated dyes also tend to migrate more, possibly due to less efficient encapsulation and more exposed surface area.

The flow rate of the polyethylene dye mixture is controlled by the pumping rate, the size of the fluid cap in the spray nozzle and the amount of air atomization pressure. With the typical nozzle arrangement (set-up #4 by spray system, fluid cap 60100, air cap 120), at 75 psi, the optimal product flow rate is about 1.5 to 2.5 kg/hour. In a production setting, a spray rate of 30 to 90 kg/hour is achievable.

It is noted that while very useful, the spray congealing process is not one-hundred percent effective. There is still a small percentage of dyes which are on the surface or near the surface that can migrate over time. Therefore, depending upon the circumstances and end use, a secondary coating, also referred to as a barrier coat, may be needed to totally eliminate dye migration. Barrier coats are well known in the pharmaceutical art. Thus, a skilled artisan would suitably use as a barrier coat the Eudragit™ series of coatings, HPMC or PVP.

Suitable secondary coatings include, but are not limited to, Petrolatum, vegetable oil, coconut oil, mineral oil, dimethicone, and pharmaceutical coatings (such as Ethyl Cellulose, or the Eudragit™ series of coatings). These coating have been successfully applied onto polyethylene encapsulated particles as a secondary coating. See Example 3 for additional information. Preferably the coating agent is Petrolatum, and mineral oil or dimethicone. Both Petrolatum, and mineral oil are effective and are also of low cost. DC Silicone Fluid™ (Dow Corning) may effect foaming properties if too much is used in certain articles, such as in a toothpaste. Use of a pharmaceutical coating, such as Eudragit™ coatings, is less preferable as it will increase cost, and will likely require either another spray drying step, or a fluidized bed coating step for such coatings. Generally, a preferred coating is made with approximately 15% matrix particles to 85% petrolatum; 50% matrix particles to 50% mineral oil and/or combinations of mineral oil and petrolatum with the matrix particles.

Particle agglomeration in spray congealing can be a problem. In every batch made there is a small percentage (0.5% to 3%) of agglomerated particles in the 65–100 micron range. These large particles can show up as dye specks in a final product, such as a gel. Preferably, these agglomerates are removed before being added into a final product that will be effected by their inclusion. A suitable means of removal is by use of an air separator or filtration, well known mechanisms to those of skill in the art.

Color matching with the polyethylene encapsulated dyes is more difficult than with soluble dyes. Starting with the same dye to polyethylene ratio, the intensity and shade of color can change from run to run depending on the process parameters. Process parameters such as product feed rate, type of fluid cap, type of air cap and atonization air pressure, all can effect the ultimate color of the encapsulated dye powder. For the same dye to polyethylene ratio, differences in color intensity and shade can be attributed to differences in particle size distribution. Small particles (<5 microns) may also be removed with an air separator or by adjusting the air pressure during the dye manufacturing.

The ratio of lake to substrate, such as polyethylene, is between about 0.5% to about 9%, preferably 2% to 6%. If the encapsulated lake is to be used "as is", i.e., without a secondary coating, a 4% lake to polyethylene ratio provides better encapsulation. If a secondary petrolatum coating is to be applied to the encapsulated particles then a higher lake to polyethylene ratio could be used. As noted below, it is possible to add more than one lake together with the substrate and then spray congeal in order to obtain the desired end product.

A drop-in homogenizer, or some other suitable high shear mixer, is needed to disperse the colored lake into the molten polyethylene. Any dye agglomerates need to be broken up and dispersed into the polyethylene for good encapsulation.

Slowly the temperature of the polyethylene-dye mixture is increased to about 125° C. and maintained at this temperature with constant agitation until the spray dryer is ready to receive the material.

The feed tank, feed line, and nozzle on the spray dryer are preferably pre-heated. While it is not necessary in all instances, depending upon the substrate chosen it is preferable for ease of manufacture and cleaning. Once the equipment is pre-heated to 125–135 ° C., the polyethylene lake mixture is poured into the feed tank. The cooling air and the atomizing air are turned on and spray congealing the mixture is begun.

The atomizing air pressure is set between 35 psi to 75 psi. Atomization pressure while variable will preferably tend to range from about 60 psi to 75 psi. The flow rate of the polyethylene dye mixture, with the typical nozzle arrangement, (spray system set-up #4, fluid cap 60100, air cap 120), at 75 psi, results in the product flow rate measuring 1.5 to 2.5 kg/hour. The pump rate for Pilot Unit will generally range from about 25 to about 40ml/min, preferably from about 25 to about 30 ml/min.

As the molten polyethylene dye mixture is atomized by the spray nozzle, fine spherical droplets are formed inside the cooling chamber. The Polywax® 500 polyethylene, for instance, has a fairly distinct solidification point at 86° C. and should follow a typical solidification curve. The polyethylene dye droplets enter the cooling chamber at about 125° C. The droplets are cooled to the solidification point (in this instance) about 86° C. Solidification takes place at constant temperature releasing heat of crystallization. After the particles are solidified, cooling continues as the particles are discharged from the cooling chamber at about 40° C. The entire cool-congeal-cool cycle occurs in a matter of seconds.

As noted above, the matrix particles produced herein may have application in cosmetics or toiletry articles, such as shower gels, mouthwashes, toothpaste or other denitrifies, for use in coatings of tablets, or to produce tablets with color where desired, i.e., pharmaceutical applications. A preferred use is in the toothpaste, mouthwash, dentifrice area or oral care.

Incorporation of the matrix particles into a desired product, such as a toothpaste formulation may be used "as is", i.e., as a fine powder which can be dispersed with the surfactant already found in toothpaste formulations, such as PEG 400, or may be dispersed with a drop-in homogenizer or a colloid mill. The matrix particles, the PEG, and the gums can be added into a batch at the beginning of the batching process. The matrix particles can also be dispersed into sorbitol using a little sodium lauryl sulfate solution and a colloid mill. It can then be added in at the thin down stage at the end of the process. It can also be added with premixed flavor and added at the end of the batch.

When the matrix particles are coated with a secondary coating of petrolatum the matrix particles are in the form of a colored paste. The colored paste may be added into the batch at the thick stage after all the thickener (e.g., Zeofree) has been charged in the batch. The dye paste may contain 15 to 25% matrix particle, 10 to 20% mineral oil and about 60 to 75% Petrolatum. If two separate matrix particles are used having different lake incorporation, the colored paste may have differing % w/w particles present to obtain the desired coloring effect. For instance, the concentration of dyes maybe 0.75% blue dye paste and 0.25% yellow dye paste.

It is recognized that there are some processing problems in utilizing the matrix particles as the fine powder form of the dye is very hydrophobic and does not readily disperse in a liquid medium. A lot of mixing energy is needed to disperse the dye, be it in PEG 400 or sorbitol. If too much heat is generated in the dispersion process (such as above 65° C.) the polyethylene coating can become soft and self agglomerate into large particles. The colloid mill used to disperse the dye is preferably cooled with ice water to keep the dispersion below 55° C. The paste form of the dye can also result in its own processing problems as it to is hydrophobic and a mixer having enough shear force may be necessary for adequate blending.

Another embodiment of the present invention is the discovery that matrix particles produced by means other than spray congealing, such as illustrated below, can be coated with a secondary coating as described herein and produce matrix particles with substantially reduced bleeding. These particles can be produced using a suitable substrate, such as high density polyethylene, with colored lakes such as FD&C Blue No.1 lake or D&C Yellow lake No.10, and ground to a fine powder, preferably 5 microns to 10 microns, preferably with a jet mill, although any available mechanism well known to one of skill in the art will suffice. The fine powder is then washed, removing any exposed dye as a result of the milling. Alternatively, the washing process can be eliminated, as applying the secondary coating of petrolatum to cover the surface will seal in any cracks to the coating.

To form the polymer matrix particle, the substrate material is first melted. In the case of high density polyethylene resin, at temperatures of about 225° F. The lake particles are stirred into the resin, such that the resultant mixture is homogeneous. Suitably, this is performed with a drop-in homogenizer, although one skilled in the art may utilize any suitable well known means. The mixture is poured onto a suitable surface, such as a metal tray, and allowed to harden, preferably at room temperature. Once cooled, the dyed polyethylene breaks away easily from the trays.

The solidified mixture is broken into pieces small enough to be fed into a suitable mill, such as a Fitzmill, producing a coarse powder of about 80 to 800 microns in size. The coarse powder is then fed into a jet mill to obtain particles about 5 microns to 10 microns in size.

Using tap water, or other water product, and filter pads, the particles are washed to remove any lake dye particles present that are exposed during the milling process. Such washing process may require 4 to 5 passes. The colored polyethylene particles are then dried, suitably air dried. The resultant product is a dry, free-flowing, dyed particle having a particle size of about 5 to 8 microns.

It is noted that the grinding and washing process may wash away about half of the original dye and accordingly this factor should be taken into account. The jet milling of the matrix particles to a fine particle size exposes the dye surfaces and causes cracks in the polyethylene matrix. The particles have to be washed to remove any exposed dye. By applying a secondary coating of a suitable material, such as petrolatum, vegetable oil, coconut oil, or a silicone fluid, onto the polyethylene encapsulated particles, the need for washing can be eliminated. The coating acts as an effective surface sealant, covering any exposed dye surfaces and sealing any cracks on the surface of the particles.

To apply the secondary coating it is preferable to disperse the jet milled particles in liquefied petrolatum using a homogenizer or colloid mill. A hydrophobic colored paste with finely dispersed encapsulated lake particles is formed after cooling to room temperature. These particles may be utilized in any of the applications as described herein. It is noted however, that particles produced in this manner will not have the uniform spherical shape of those particles as produced by the spray congealing method herein. However, for certain applications where a small uniform shape is not necessary, such as speckles in deodorants or soaps, these methods can produce a suitable product. As with the spray congealing method the substrate-lake is recyclable.

The following examples are intended to illustrate the invention and are not intended to limit the scope thereof. In the examples, all parts and percentages are by weight unless otherwise specified.

EXAMPLE 1

Spray Congealing

Specifically utilizing FD&C Blue No. 1 Aluminum lake and Polyethylene (Polywax® 2000, Petrolite) and utilizing similar conditions to those indicated above the following process took place:

Polyethylene was first melted using a Glas-col Heating Mantle equipped with an automatic temperature controller. When the polyethylene was completely melted, approx. 130–135° C., the aluminum lake was dispersed in the liquid polyethylene with the aid of a high-shear homogenizer, such as a Silverson homogenizer. This dispersion takes about 15 minutes. The dispersion was then homogenized for an additional 30 minutes to insure that the lake was uniformly dispersed in the polyethylene. The mixture was maintained at a temperature of about 125–135° C. at all times. When a uniform dispersion was attained, the mixture was then charged into a suitable delivery unit, which are optimized for the particular substrate chosen. In this instance, the tank temperature was about 280° F.; the hose temperature about 310° F.; the head temperature about 330° F.; the pump rate about 7 to 10%; and the atomization pressure about 68–75 psi.

The material was then collected and the yield recorded. The crude material was then air classified to obtain the desired or usable fraction (in this instance about 5–15 $\mu$m).

Using the above experimental procedures spray congealed dye colors manufactured were blue and aqua The blue was obtained using FD&C Blue No. 1 aluminum lake. In one experiment the percentage blue lake was 6%.

For an aqua color, a mixture of Blue No. 1 aluminum lake and D&C Yellow No. 10 aluminum lake was utilized. The percentage of blue lake was 2.28% and 1.72% yellow lake.

In additional experiments using the same conditions the percentage of Blue No. 1 lake varied from 2.28 to 8.49%. Similarly, matrix particles were obtained using Yellow No.10 dyes ranging from 1.24 to 2.91 %. The tank temperatures varied from 280 to 300° C.; the hose temperatures from 300 to 3 10° C.; the head temperatures from °F. initially of about 310 to 335°; the pump rates varied from about 7.5% to up to 30%; the atomizing pressure (psi) ranged from 15/20 to up to 70/76.

EXAMPLE 2

Spray Congeal Process

Using analogous methods to those indicated above except for the substrate being Polywax® 500 from Petrolite and FD&C Blue No.1 lake 12% was used. Alternatively, another example was performed using D&C Red No.10 lake 18%. The two colors were kept separate in this experiment, although it is recognized that it is possible to add both the blue lake and the red lake together to the polyethylene at this stage and spray congeal to obtain the desired color.

The spray dryer used herein had a capacity of 2–5 Kg/hr. [Generally, a batch size is about one Kg which is about ½ hour running time in the dryer.]

Slowly the temperature of the polyethylene-dye mixture in this experiment was increased to about 125° C. and maintained at this temperature with constant agitation until the spray dryer was ready to receive the material.

The feed tank, feed line, and nozzle on the spray dryer were pre-heated. Once the equipment is pre-heated to 125–135° C., the polyethylene lake mixture was pumped into the hopper. The cooling air and the atomizing air were turned on and spray congealing the mixture was begun.

The atomizing air pressure was set between 35 psi to 75 psi. The flow rate of the polyethylene dye mixture, with the typical nozzle arrangement, (spray system set-up #4, fluid cap 60100, air cap 120), at 75 psi, resulted in the product flow rate measuring 1.8kg/hour. The pump rate was set at 30ml/min (Cole-Parmer, MasterFlex peristack pump, size 25, silicone tubing).

As the molten polyethylene dye mixture was atomized by the spray nozzle, fine spherical droplets were formed inside the cooling chamber. The polyethylene-dye droplets enter the cooling chamber at about 125° C. The droplets were cooled to the solidification point of about 86° C. Solidification takes place at constant temperature releasing heat of crystallization. After the particles were solidified, cooling continues as the particles were discharged from the cooling chamber at about 40° C. The entire cool-congeal-cool cycle happens in a matter of seconds.

In alternative experiments, using a heated tracedline and nozzle, as well as a feed pot on a hot plate, Polyethylene (Polywax® 500) was used with a combination of 3.6% Blue and 1.2% yellow colored lakes; with a combination of 3.6% Blue and 0.6% yellow colored lakes; and with a combination of 0.435% Blue and 0.065% yellow colored lakes.

Another polyethylene substrate, in this instance a high density polyethylene (Acumist C, Allied Signal) grade was used with a combination of lakes 3.6% Blue and 0.6% yellow colored lakes.

In addition to polyethylene, both Mekon White Wax™ (Microcrystalline Wax) was used with a combination of 3.6% Blue and 0.6% yellow colored lakes. Also natural Carnauba Wax with a combination of 3.6% Blue and 0.6% yellow colored lakes; a combination 1.8% Blue and 0.3% yellow colored lakes; and a combination of 6.9% Blue and 0.6% yellow colored lakes was successfully made. Carnauba Wax synthetic was also used as a substrate (Petronauba) with a combination of 3.6% Blue and 0.6% yellow colored lakes. As previously described, the lakes were combined, to obtain the desired color, in the hot melt.

In yet another embodiment of the present invention, a combination of substrates were used with varying % blue lakes: polyethylene and Carnauba Wax (equivalent amounts) with a 3% blue lake; a 4:1 ratio of polyethylene to Mekon White™ Wax with a 3% blue lake and a 4:1 ratio of polyethylene to Mekon White™ Wax with a 2% blue lake; a 9:1 ratio of polyethylene to Mekon White™ Wax with a 3% blue lake; Mekon White™ Wax alone with 3% Blue lake; and polyethylene alone with 1.0% lake.

EXAMPLE 3

Secondary Coating of Matrix Particles

Utilizing the above prepared matrix particles from Example 1 a secondary coating of hydrogenated vegetable oil (Creamtex, Van den Berg) was applied. Batches made with this material showed some improvement over bleeding or leaching than those particles made with primary color alone.

In an alternative experiment coated matrix particles, approx. 15% w/w were coated with 85% w/w petrolatum. The matrix particles coated with the Polywax® 500 with 3.6% Blue/0.6% yellow; the high density polyethylene (Acumist C Grade) as made in Example 2 above; and the three natural Carnauba Wax substrates also made in Example 2 above.

In an alternative experiment also made were mineral oil and DOW silicone fluid coatings on polyethylene matrix particles:

Example 3(ii)

50 gms of Kaydol™ mineral oil were mixed with 50 gms of the matrix particles in a beaker and mixed with a spatula for about 5 minutes to form a cream mixture. The matrix particles were prepared in accordance with the process herein and contained 800 gms Polywax®500, 17 gms 12% blue lake, 5 gms blue lake (40%) and 2 gms yellow lake.

Example 3(iii)

Using 50 gms Dimethicone (Dow Corning, 200 Fluid), and 50 gms of matrix particles as described in Example 3(ii) above, were mixed.

Example 3(iv)

Using a combination of petrolatum and mineral oil, in a ratio of 1200 gm of petrolatum to 150 gm of snow white mineral oil were mixed together and heated to 52° C., then 300 gms of matrix particles (as described in Example 3(ii)) were charged and mixed with the secondary coating in a homogenizer for about 30 minutes, and cooled to room temperature.

EXAMPLE 4

Toothpaste Processing

Using the procedure noted above in the specification, and in Example 3, a paste was made in both a Ross mixer and a Nauta mixer using both blue matrix particles (approx. 0.53%) and yellow matrix particles (0.17%) for a total of 0.7% matrix particles.

The paste was added to a general toothpaste formulation (e.g., as can be found in U.S Pat. No. 4,340,583, issued Jul. 20, 1982, to Wason; and U.S. Pat. No. 5,094,843, issued Mar. 10, 1992, to Mazzanobile et al.), a typical formulation being described below, by first incorporating the matrix particle paste into the gum component and then mixing as normal.

| Raw Material | Percent W/W Range |
| --- | --- |
| Sorbitol 70%, USP | 20 to 50 |
| Glycerin 99.5%, USP | 00 to 30 |
| Abrasive | 10 to 20 |
| Thickening Silica, FCC | 10 to 20 |
| Polyethylene Glycol, NF | 0 to 5 |
| Fluoride Ion Source | 0.2 to 0.85 |
| Detergent | 1 to 3 |
| Flavor | 0.5 to 1.5 |
| Sweetener | 0.15 to 0.25 |
| Thickener | 0.8 to 1.5 |
| Preservative | 0.1 to 0.2 |
| Spray Congealed Dye | 0.01 to 0.10 |
| Dye/Dyes | 0.001 to 0.01 |
| Deionized Water | QS to 100.00 |

As will be recognized by the skilled artisan, suitable abrasives for use herein are calcium carbonate, dicalcium phosphate dihydrate or silica; a suitable fluoride ion source for use herein is sodium monofluorophosphate or sodium fluoride; a suitable sweetener is sodium saccharin; a suitable detergent is sodium lauryl sulfate; and a suitable preservative is sodium benzoate.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows:

What is claimed is:

1. A process for forming an encapsulated matrix pigment particle which process comprises:
   a) heating a substrate to a molten liquid state;
   b) adding one or more colored lakes or dyes to said molten liquid to form a substrate:lake mixture; and c) maintaining the temperature of the substrate:lake mixture and spray congealing the mixture to yield a fine particle distribution of encapsulated matrix pigment particles upon cooling.

2. The process according to claim 1 wherein the colored lake or dye is added to the substrate prior to heating to a molten liquid state.

3. The process according to claim 1 wherein the ratio of lake to substrate is from about 0.5 to 9 percent.

4. The process according to claim 3 wherein the ratio of lake to substrate is from about 1 to 6 percent.

5. The process according to claim 1 wherein the substrate:lake mixture is fed into a cooling chamber and atomizing air added.

6. The process according to claim 5 wherein the cooling chamber feeds into a cyclone for means of collecting the matrix pigment particles.

7. The process according to claim 6 wherein the matrix pigment particles are further collected in a filter bag.

8. The process according to claim 7 wherein the particles are air classified.

9. The process according to claim 1 wherein the matrix pigment particle is between about 5 and 35 microns in size.

10. The process according to claim 9 wherein the matrix pigment particle is between about 5 and 15 microns in size.

11. The process according to claim 1 wherein the substrate is polyethylene, hard microcrystalline wax, or Carnauba Wax.

12. The process according to claim 1 wherein the colored lake is FD&C Blue No.1, Yellow No.10, or Red No.10.

13. A matrix pigment particle produced according to claim 1.

14. The matrix pigment particle according to claim 13 which comprises a ratio of lake to substrate of from about 0.5 to 9 percent.

15. The matrix pigment particle according to claim 13 wherein the substrate is polyethylene, hard microcrystalline wax, or carnauba wax.

16. The matrix pigment particle according to claim 14 wherein the colored lake is FD&C Blue No.1, Yellow No.10, or Red No.10.

17. The matrix pigment particle according to claim 13 which is between about 5 and 35 microns in size.

* * * * *